(12) United States Patent
Hummer et al.

(10) Patent No.: US 12,322,266 B2
(45) Date of Patent: *Jun. 3, 2025

(54) MONITORING CHEMICALS AND GASES ALONG PIPES, VALVES AND FLANGES

(71) Applicants: Gregory J. Hummer, Shaker Heights, OH (US); Matthew Hummer, Atlantic Beach, FL (US)

(72) Inventors: Gregory J. Hummer, Shaker Heights, OH (US); Matthew Hummer, Atlantic Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/372,311

(22) Filed: Sep. 25, 2023

(65) Prior Publication Data

US 2024/0013646 A1  Jan. 11, 2024

Related U.S. Application Data

(63) Continuation of application No. 17/330,524, filed on May 26, 2021, now Pat. No. 11,769,389, which is a
(Continued)

(51) Int. Cl.

| | |
|---|---|
| *G08B 21/12* | (2006.01) |
| *G08B 21/14* | (2006.01) |
| *G08B 21/16* | (2006.01) |
| *G08B 25/08* | (2006.01) |
| *H04B 1/3888* | (2015.01) |
| *H04M 1/72412* | (2021.01) |
| *G01N 33/00* | (2006.01) |
| *G01N 33/497* | (2006.01) |

(Continued)

(52) U.S. Cl.
CPC ............. *G08B 21/12* (2013.01); *G08B 21/14* (2013.01); *G08B 21/16* (2013.01); *G08B 25/08* (2013.01); *H04B 1/3888* (2013.01); *H04M 1/72412* (2021.01); *G01N 33/0009* (2013.01); *G01N 33/4972* (2013.01); *G08B 25/10* (2013.01); *H04M 1/21* (2013.01)

(58) Field of Classification Search
CPC ........ G08B 21/12; G08B 21/14; G08B 21/16; G08B 25/08; H04M 1/72412; H04B 1/3888
USPC ..................................................... 340/539.11
See application file for complete search history.

(56) References Cited

U.S. PATENT DOCUMENTS

| | | | |
|---|---|---|---|
| 8,629,770 B2* | 1/2014 | Hummer | G08B 25/012 340/539.1 |
| 8,930,341 B2* | 1/2015 | Amin | G06F 16/2455 707/706 |

(Continued)

*Primary Examiner* — Kerri L McNally
(74) *Attorney, Agent, or Firm* — Lippes Mathias LLP

(57) ABSTRACT

Detection and real-time reporting (via wireless to a remote receiver) of the release of harmful or otherwise unwanted chemicals or chemicals of corrosion into the environment and, more particularly, the undesired release of such chemicals from pipelines, supporting energy/electric/heating/cooling/storage/distribution infrastructure, refineries, chemical plants, factories, processing and manufacturing plants and equipment, storage tanks, engines, containers and the like. One or more detection devices can be placed nearby potential areas where leaks occur, or anywhere monitoring for leaks is desired. In some embodiments, the detection devices are integrated into components for monitoring said component for unwanted emissions.

20 Claims, 16 Drawing Sheets

Related U.S. Application Data continuation of application No. 16/696,136, filed on Nov. 26, 2019, now Pat. No. 11,024,146, which is a continuation of application No. 15/914,025, filed on Mar. 7, 2018, now Pat. No. 10,490,053, which is a continuation-in-part of application No. 15/891,410, filed on Feb. 8, 2018, now Pat. No. 10,395,503, which is a continuation of application No. 15/235,981, filed on Aug. 12, 2016, now Pat. No. 9,922,525.

(60) Provisional application No. 62/297,385, filed on Feb. 19, 2016, provisional application No. 62/205,012, filed on Aug. 14, 2015.

(51) Int. Cl.
*G08B 25/10* (2006.01)
*H04M 1/21* (2006.01)

(56) References Cited

U.S. PATENT DOCUMENTS

| | | | | |
|---|---|---|---|---|
| 10,490,053 | B2* | 11/2019 | Hummer | G08B 21/12 |
| 11,024,146 | B2* | 6/2021 | Hummer | G08B 21/12 |
| 11,061,009 | B2* | 7/2021 | Hummer | G08B 21/08 |
| 11,769,389 | B2* | 9/2023 | Hummer | G08B 21/14 |
| | | | | 340/539.11 |
| 11,963,517 | B2* | 4/2024 | Hummer | A01K 47/06 |
| 2006/0049714 | A1* | 3/2006 | Liu | G01S 13/755 |
| | | | | 310/313 R |
| 2014/0349707 | A1* | 11/2014 | Bang | G08B 21/12 |
| | | | | 455/556.1 |
| 2015/0077737 | A1* | 3/2015 | Belinsky | G01N 15/0211 |
| | | | | 250/208.2 |

\* cited by examiner

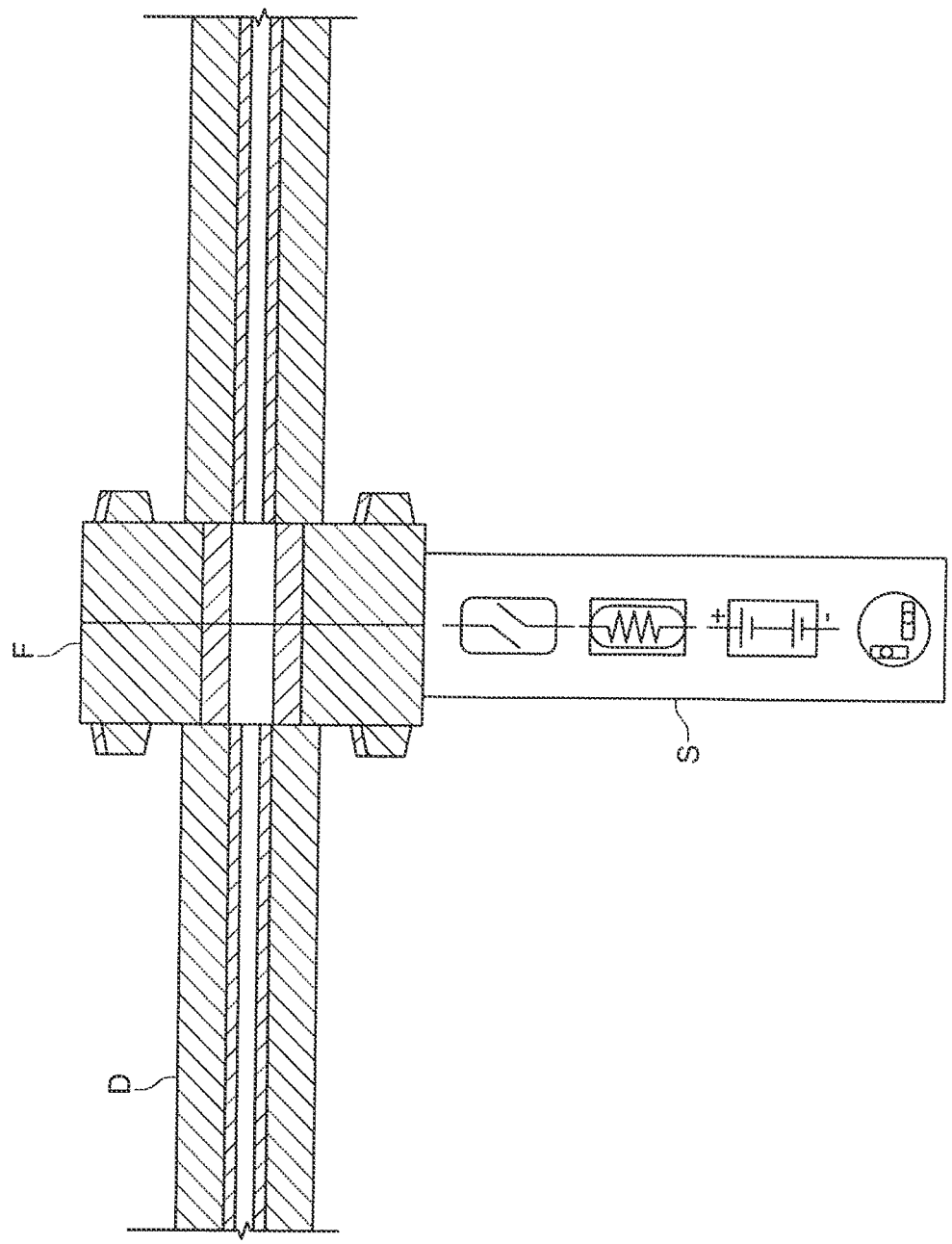

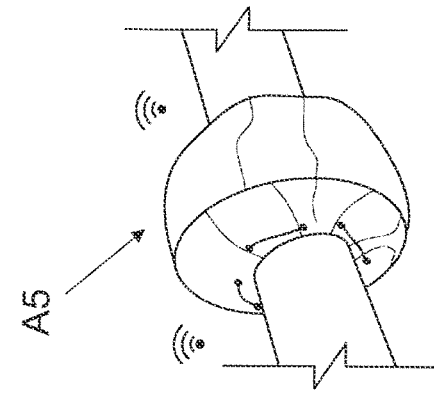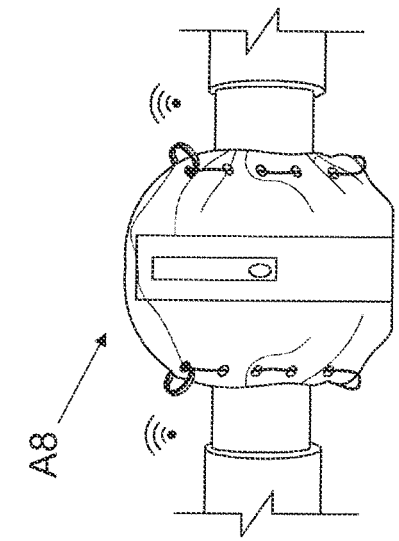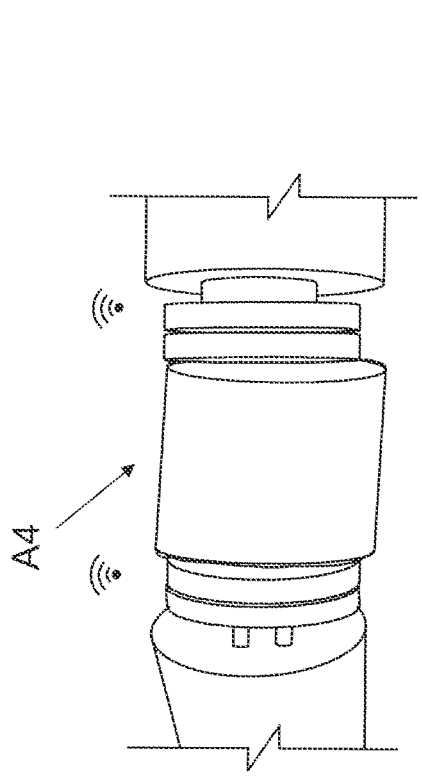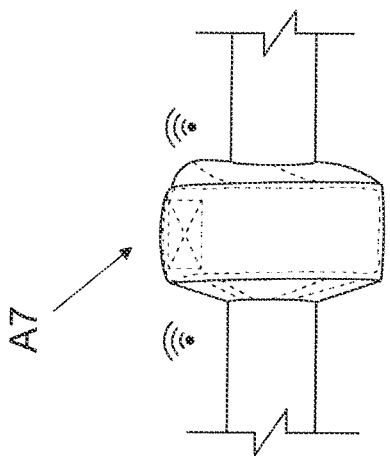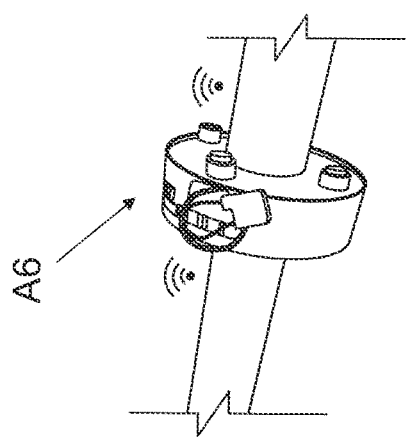
FIG. 11
FIG. 12
FIG. 13
FIG. 14
FIG. 15

MONITORING CHEMICALS AND GASES ALONG PIPES, VALVES AND FLANGES

CROSS REFERENCE TO RELATED PATENTS AND APPLICATIONS

The present application is a continuation of U.S. patent application Ser. No. 17/330,524, filed May 26, 2021, which is a continuation of U.S. patent application Ser. No. 16/696,136, filed Nov. 26, 2019, now U.S. Pat. No. 11,024,146, which is a continuation of U.S. patent application Ser. No. 15/914,025, filed Mar. 7, 2018, now U.S. Pat. No. 10,490,053, which application is a continuation in part of patent application Ser. No. 15/891,410, filed Feb. 8, 2018, now U.S. Pat. No. 10,395,503, which is a continuation of U.S. patent application Ser. No. 15/235,981, filed Aug. 12, 2016, now U.S. Pat. No. 9,922,525, which application claims the benefit of U.S. Provisional Patent Application Ser. No. 62/297,385, filed Feb. 19, 2016, U.S. Provisional Patent Application Ser. No. 62/205,012, filed Aug. 14, 2015, and U.S. Provisional Patent Application Ser. No. 62/468,072, filed Mar. 7, 2017, which applications are hereby incorporated by reference.

FIELD

The present exemplary embodiment relates to systems and methods for detecting chemicals or gasses including chemicals produced by corrosion. It finds particular application in conjunction with detecting chemical signs of corrosion or leaks from pipelines, valves, pressure fittings, pump, plugs, gauges, connectors, compressors, open-ended lines, pipe joints, couplings and other fluid transmission components and storage containers etc., and will be described with particular reference thereto. However, it is to be appreciated that the present exemplary embodiment is also amenable to other like applications.

BACKGROUND

The Environmental Protection Agency (EPA) has determined that leaking equipment, such as valves, pumps, and connectors, are the largest source of emissions of volatile organic compounds (VOCs) and volatile hazardous air pollutants (VHAPs) from petroleum refineries and chemical manufacturing facilities. A typical refinery or chemical plant can emit 600-700 tons per year of VOCs from leaking equipment. Accordingly, Leak detection and repair (LDAR) is an important part of reducing environmental contamination from such facilities.

The EPA has set forth standards and guidance on determining such leaks of VOCs and HAPs through a framework known as Method 21. This Method applies to, but is not limited to, valves, flanges and other connections, pumps and compressors, pressure relief devices, process drains, open-ended valves, pump and compressor seal system degassing vents, accumulator vessel vents, agitator seals, and access door seals. The Method establishes the type of instrumentation, equipment and supplies that can be used to monitor leaks; it also defines concentration standards for measuring emissions by equipment type; it defines how samples should be collected, tested and reported; it also establishes a protocol for quality control as well as criteria for auditing facilities and how they conduct LDAR.

LDAR for chemical processing plants, such as refineries, is typically performed by trained personnel. The trained personnel are tasked with physically inspecting and sampling a wide variety of valves, pipe flanges, compressors, etc. for leakage on a periodic basis. This typically includes taking measurements with a handheld chemical detector. Current LDAR programs are labor intensive, time consuming, and have been found by the Environmental Protection Agency (EPA) to rarely be properly implemented by plant operators. The proper implementation is something that the agency aggressively pursues with its oversight along with other state and local regulators.

The failure of plant operators to properly implement a LDAR program, in many cases, is due primarily to the overwhelming expense, record-keeping and complexity such programs require. The expense comes not only from the physical labor involved with visiting and testing each component for leakage, but with keeping track of acceptable leakage rates for the wide variety of components and varying standards that exist in a typical plant, such as a refinery.

For example, each type of valve may have its own acceptable leakage threshold. For each given type of valve, each size of that type of valve may have a different acceptable leakage threshold. Further, newer valves may have different acceptable leakage thresholds than older versions of the same valve. The same challenges exist with other components such as compressors, connectors, sampling ports, etc. Thus, the record keeping required to track all components and their respective acceptable leakage thresholds presents a significant challenge as plant components are replaced and/or updated. Leakage thresholds also depend on the type of analyzers used and their respective detection capability. As a result, matching analyzing equipment standards with those for which they are monitoring is extremely challenging when dealing with thousands and in some cases millions of components.

Therefore, the trained personnel must not only sample each component, but must also determine the acceptable leakage threshold for the sampled component based on documented standards and best practices. A significant risk of error is misidentification of a given component (and/or acceptable leakage threshold). Risk of error also exists when sampling, as human operators may misuse the equipment or the equipment may not be calibrated properly.

U.S. Pat. No. 7,176,793 discloses a detection device in the form of a strip for use in an enclosed container. The detection strip includes sensors of macro, meso or nanosize, all of which are referred to as nanosensors, for detecting materials that are harmful to human beings within an enclosed container and for transmitting a corresponding resonance frequency. One or more detection strips are initially placed within a container, depending on the size of the container. Other types of nanosensors including those that detect temperature, humidity, location and other conditions can also be part of the sensor array. The detection devices are designed to send off specific resonant frequency signals which can be detected by voltage changes and/or current changes which are correlated to any harmful material detected within the container. In some applications, sensors can be located in open air and can be configured to receive and sample a forced air flow. A serial number computer chip is provided for specifically identifying the detection device and transmitting a corresponding resonance frequency, which allows the container to be identified. A power source is provided for operating the detection strip. A hand-held or stationary monitor is provided for monitoring the container for any signals given off from the detection strips within the container. The detection devices are designed to give off a predetermined amount of background signal. In consequence, if no such signals are received, the container is highly suspect as being tampered with, allowing such a container to be quickly removed and its contents examined.

SUMMARY

Aspects of the present disclosure are directed to methods, processes, tactics, systems and devices for transforming the manual LDAR process to an automated and digitized LDAR process that is more effective at a lower cost, thus reducing pollution while saving plant operators money. In one embodiment, aspects of the present disclosure combine "digital transformation" and the Internet of Things (IoT) or Machine to Machine Communication. The present disclosure allows the core task of monitoring leaks and tracking progress in that task, but also collects data that is highly valuable to broader business operations, specifically on-going maintenance and repair. The data can go as far as becoming a critical input to refinery operations KPIs that are disclosed to the public. The purpose of showing in KPIs would be two fold: i) provide an indication of how well a company manages its programs associated with public "externalities" (i.e. emissions of VOCs and HAPs) ii) provide an indication how the proper and efficient management of those programs lead to more efficient production, reducing product losses through unwanted emissions and the level of safety for facility workers and infrastructure operators. Insight into how a publicly traded company is handling leak detection and repair (LDAR) will provide greater evidence to regulating agencies and bodies and may ultimately lead to avoiding enforcement actions and fines.

Aspects of the present disclosure relate generally to the detection and real-time reporting (via wireless to a remote receiver) of the release of harmful or otherwise unwanted chemicals or chemicals of corrosion into the environment and, more particularly, the undesired release of such chemicals from pipelines, supporting energy/electric/heating/cooling/storage/distribution infrastructure, refineries, chemical plants, factories, processing and manufacturing plants and equipment, storage tanks, engines, containers and the like. The present disclosure sets forth one or more detection devices which are placed nearby potential areas where leaks occur, or anywhere monitoring for leaks is desired. In some embodiments, the detection devices are integrated into components for monitoring said component for unwanted emissions. The detection devices are designed not only to detect the presence of a particular chemical, but also its level (e.g. in parts per million, parts per billion, or parts per trillion, etc.). Detecting levels of emissions of unwanted chemicals or gases will help guide operators' planning of maintenance and repair as well as broader LDAR activity.

In essence, the present disclosure sets forth a system and method for automated detection, processing and/or decision making associated with chemicals of corrosion or leaks of harmful chemicals at refineries, chemical plants and/or any other facilities having infrastructure prone with leak potential. The automated detection is based on generating data that previously could not be generated by manual approach using a network of sensors, and processing that data for accurate and real-time automated decision making related to a specific set of defined criteria that can be programmed to the device.

The new automated process in accordance with the present disclosure displaces and/or augments existing manual LDAR techniques whereby human operators are required to test hundreds of thousands or millions of areas prone to leaks using hand-held samplers as shown, (e.g., see, for example, FIG. 20). Each piece of equipment has a different standard and the standards vary by the model and brand of equipment. The present disclosure facilitates automated sampling that not only detects whether a piece of equipment is emitting past a minimum baseline concentration and a maximum standard, but also the varying levels between, which are likely to be a result of utilization and overall plant productivity. This type of reporting generates useful data for not only measuring plant utilization level and the stress being placed on related component equipment, but also shows how that level or operation contributes to levels of unwanted emissions.

Aspects of the disclosure can provide managers of infrastructure and other facilities involving harmful or other chemicals information regarding when, where and at what level the harmful or other chemicals are present. A network of remote sensors powered by batteries, solar power or by electromagnetic energy via an antenna from the wireless network can communicate wirelessly with hand-held devices and/or terminal stations to allow for real-time leak detection and analysis, planning and decision making. Open source stations for receiving, processing and analyzing sensor data are also contemplated.

This disclosure further sets forth methods and devices for fixating or otherwise mounting sensors (e.g., nano-tube sensors) to or within proximity to components prone to corrode or leak throughout pipeline infrastructures such as refineries, factories, chemical plants, processing and manufacturing facilities and water treatment facilities. In some embodiments, the sensors are integrated into with equipment and components prone to unwanted emissions or leaks. The present disclosure facilitates the detection of harmful or other chemicals that would prove dangerous or undesirable to human operators and broader facility operations, the environment, humans and more broadly business operations.

The system can include flexible strips, magnetic, adhesive, hook-and-loop or similar structures capable of permanent or temporary fastening to a pipe, flange, valve or other structure (e.g., a weld). The flexible strips are embedded with one or more of nano-sensors, a power source (including a lithium ion (or other) battery and/or powered by electromagnetic energy via an antenna from the wireless network and/or solar cell capabilities, solar power being especially useful for sensors in remote areas such as gas pipelines and hard to reach areas of factories where replacement due to failing power source would be challenging), humidity and temperature sensors (can be used to actively calibrate the passive sensors due to the environment in which the sensor is operating) and circuitry to communicate wirelessly with hand-held devices and terminals. The sensors are placed nearby sources of potential corrosion or leaks (e.g., unwanted emissions) including, but not limited to: pumps, valves, connectors, sampling connections, compressors, pressure relief devices, open-ended lines, welds, pipe joints and couplings, plugs, gauges, tanks, engines, storage containers and other energy infrastructure, plant and equipment carrying harmful or expensive gases (e.g., gases with monetary value or core to business model) and/or chemicals where leaks or emissions are not wanted, etc.

Depending on the particular application, the sensors can be embedded in either a flexible strip, foam or sponge or other material that can be wrapped in durable fabric capable of withstanding extreme temperatures, humidity and other harsh conditions and fastened to a pipe flange using hook-and-loop fasteners, elastic, pins, magnets, insulation, neoprene, polyethylene foam, advanced composites and plastics, rubber, fiberglass acrylic industrial adhesive tape, or other securements. The durable and temperature resistant fabric can have a small power source light and/or other indicators visible when the system is installed to indicate whether the sensor is functioning (e.g., sensor self-reports its state of operability) or to indicate other functions/operations. These same functions can be transmitted via the wireless circuitry to a wireless receiver or smart phone, wearable device, etc.

A similar approach can be taken for valves, pressure relief devices, welds and pipe joints. For valves, a bonnet of plastic or other suitable material (e.g., durable fabric including nano-fabrics made of graphene or other particles of the nano scale) with elastic can be stretched over the valve body and/or actuation member (e.g., knob, lever, handle, electromechanical actuator, etc.). In some examples, the bonnet material itself can be elastic and made of material with embedded sensors including nano-fabrics. In other examples, the bonnet material may be substantially inelastic and a separate elastic member can be provided to allow an opening of the bonnet to be stretched over structures such as valves, for example. The bonnet material can support the sensors and or a light or other indicator that indicates whether the sensors are functioning.

The sensor component can use nano-particle, doped nanotube, nano-tube, nanowire or other nano-type designs including nanofilm, nanocages, nanochains, nanocomposites, nanofabrics, nanofibers, nanoflakes, nanomesh, polymers, graphene or other carbon form of the nanoscale to monitor for chemical leaks along pipes, valves, flanges, welds or other areas for the purposes of safety monitoring such as in refineries, chemical plants, exhaust systems, engines, rocket motors, other pipes, fittings and connections and storage tanks, for example. In some examples, Microelectrochemical systems (MEMS) and/or Nanoelectromechanical systems (NEMS) can be used. In some examples, quantum dots or graphene quantum dots can be used. In still other examples, electrochemical, electrochemical amperometric, metal oxide semiconductor, infrared sensor (nondispersive), thermal sensor (pellitor), photoionization (PID), chemoresistors, graphene, hybrid and nanostructures, Quartz Microbalance, and/or field-effect transistor (FET) type devices can be used.

The device can consist of a nano sensor or array of nano sensors that are connected to a potentiostat, amplifier, analog to digital converter ADC, an analyzer microprocessor (CPU) and a memory that contains algorithms, which can be downloaded from a central source, that allow the sensors to differentiate multiple chemicals and gases. The sensors communicate with the CPU/memory and then report their findings via a data-link, standard wireless connection, near-field, bluetooth or other wireless connection which can be encrypted, if desired.

Each sensor or array of sensors can have an exclusive encrypted serial number which is reported along with the sensing data to a common data collector, which can be a wireless device or other centralized collector.

The sensor or array of sensors also can contain additional sensors for temperature, humidity and/or location, such as a GPS locator circuit such that a refinery having hundreds or thousands or millions of sensors can be displayed on screen in a multi-dimensional picture of the entire refinery's potential leak areas. The sensors can report the level of emission and compare the level to an established baseline of a newly installed piece of equipment (e.g., to the standard established by the LDAR Program by which emission cannot exceed without requiring replacement). Analytics can be used to display the level as well as other plant and equipment utilization indicators like pipe pressure, temperature, vibration and other metrics that provide an indication of utilization and the stress the level of utilization poses for the infrastructure. All of these metrics, particularly the leak detection metric, help operators plan maintenance and repair for optimal production and mitigate enforcement actions from regulators.

The sensor or sensor array and all electronics can be embedded in a magnetic disc, elastic covering or other shape that can be directly affixed or built directly into or in a compartment of the flange, pipe or area to be monitored for leaks.

In another example, the sensor or sensor array and electronics are embedded in a non-metallic, non-magnetic structure that can be affixed to the area to be monitored by adhesive, strapping or elastic. Other possibilities exist including using a temperature resistant heavy duty wrap with industrial Velcro or other fastener. This approach combines industrial grade composites resistant to extreme temperature and conditions. Another approach includes the use of an industrial grade nanofabric with embedded sensors. The fabric is fastened using a draw string. Similarly, the sensors can be enclosed in a durable, extreme condition-resistant wrap, but breathable bag that allows the sensors to operate without causing corrosion. A standard adjustable elastic flange covering packed with the sensor strips can be deployed. In another embodiment, a casing made of advanced composites or other materials suitable for such application can be secured around the pipe flange and secured with a standard clasp lock.

The sensor or sensor array can be replaceable within the overall sensor device. The entire device can have a red (or other color) LED light that illuminates when the entire sensor array needs to be replaced. The same light can blink when just the sensor array within the device needs to be replaced. These same two signals can also be sent by wireless to a wireless device or central monitoring device. The unit can be powered by either a small battery or directly via wireless energy via an antenna or by solar energy.

BRIEF DESCRIPTION OF THE DRAWINGS

FIG. 3 is a side view of an exemplary pipe flange having a sensor in accordance with the present disclosure;

FIG. 11 is a side elevation view of an exemplary flange band in accordance with the present disclosure;

FIG. 12 is a side elevation view of an exemplary flange band in accordance with the present disclosure;

FIG. 13 is a side elevation view of an exemplary flange band in accordance with the present disclosure;

FIG. 14 is a side elevation view of an exemplary flange band in accordance with the present disclosure;

FIG. 15 is a side elevation view of an exemplary flange band in accordance with the present disclosure;

DETAILED DESCRIPTION

Figure 1:
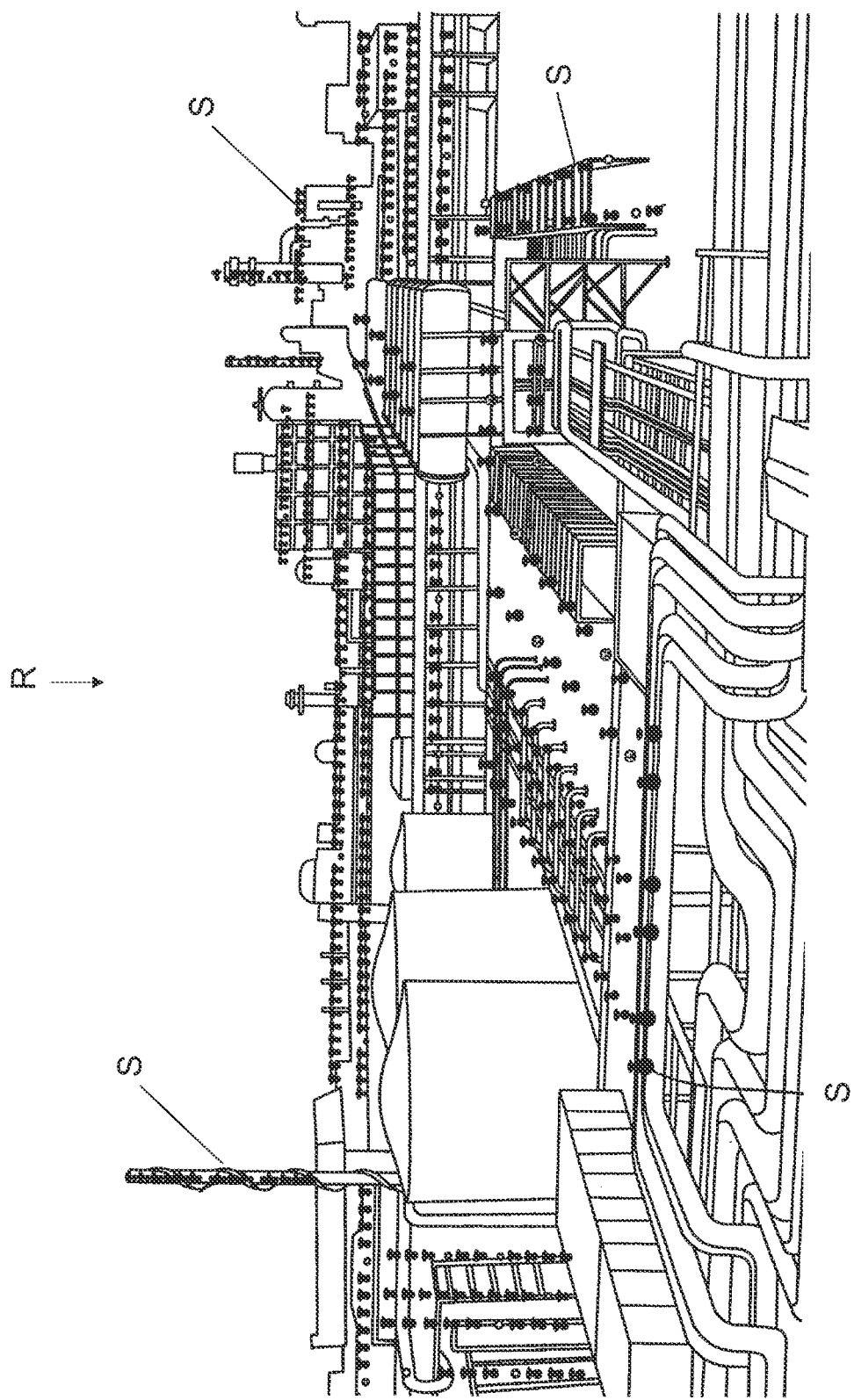
FIG. 1 is a perspective view of an exemplary chemical processing plant including a system in accordance with the present disclosure.

With reference to FIG. 1, an exemplary refinery R (or other facility) is illustrated with a plurality of sensors S (shown as small black and grey circles) mounted to various components in accordance with the present disclosure. The sensors S are connected together with one or more receivers for receiving data generated by the sensors S. As will be appreciated, the network may be a mesh network, star network, or any other type of network. Each sensor S is adapted to transmit data relating to one or more of the presence and/or concentration of one or more chemicals, sensor status/health, power supply condition, etc. Each sensor can include an indicator for indicating proper function, such as a led light or the like. The chemicals can be liquid or gaseous chemicals.

Figure 2:
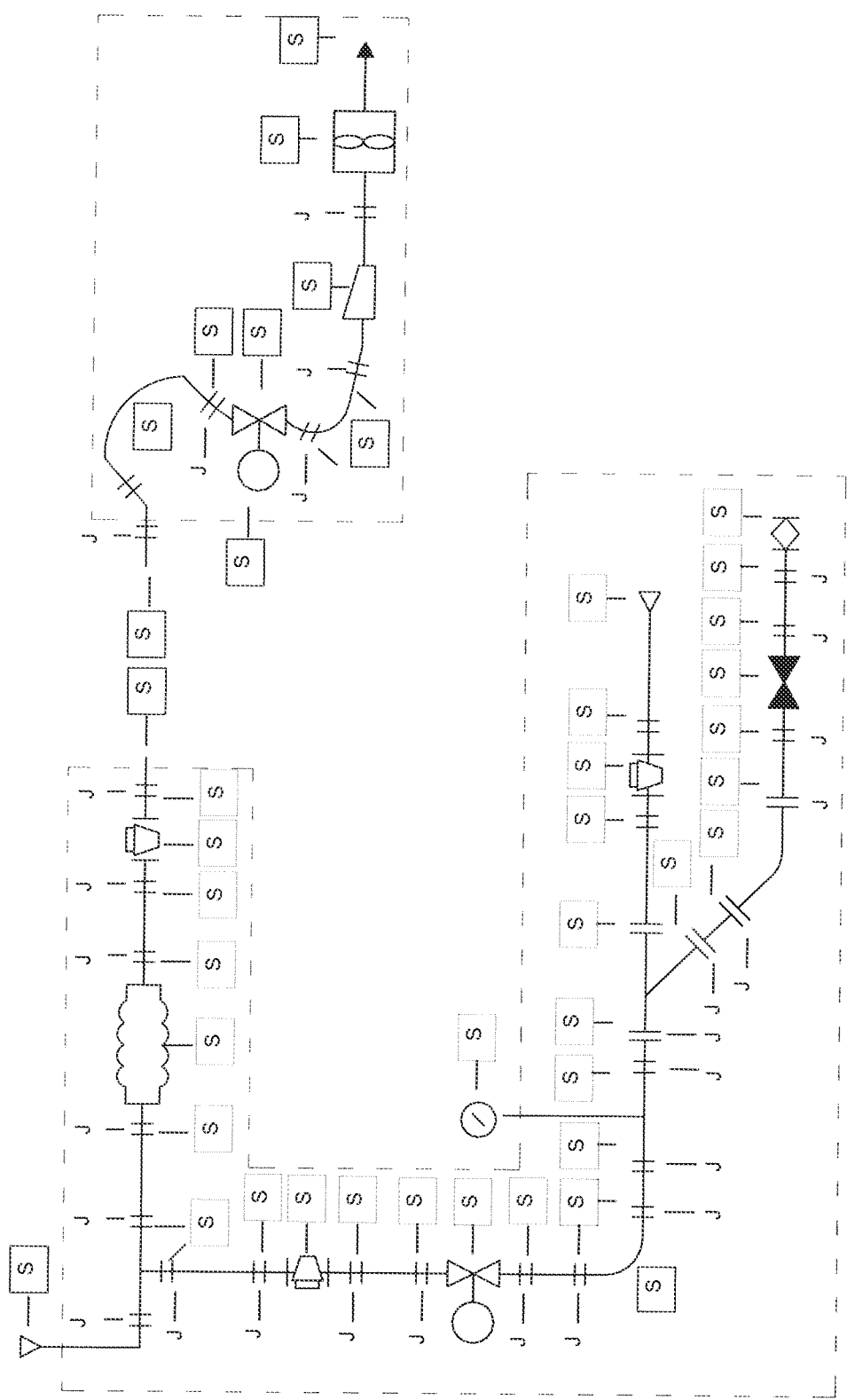
FIG. 2 is a schematic view of a portion of the plant of FIG. 1 illustrating various components and sensors for detecting leakage.

FIG. 2 schematically illustrates a fresh air inlet portion of the refinery R. It will be appreciated, however, that the principles disclosed in connection with the fresh air inlet portion of the refinery R are applicable to virtually any other portion of the refinery. The fresh air inlet generally comprises a plurality of components including a gauge cock A, a motorized valve B, a flanged elbow C, a pressure readout D, a locked valve E, a plug F, an expansion joint G, an eccentric reducer H, a turbine I and a number of pipe connectors J.

Many, if not all, of the components of FIG. 2 are monitored for unwanted emissions by a plurality of sensors S positioned in proximity to the components. The sensors S are typically mounted directly to the components via various mounting/attaching mechanisms (examples described below) that support the sensors S in a suitable location for sampling. In some applications, the sensors can be supported by structure adjacent to the component. The sensors can also be built directly into the components or in a compartment of the component being monitored for emission.

Turning to FIG. 3, an example pipe P and pipe flange F (e.g., pipe connector J, as shown in FIG. 2) are illustrated including an exemplary sensor S shown schematically in proximity thereto in accordance with the present disclosure. The sensor S can be integrated with the flange F (e.g., provided as part of the flange F by the flange manufacturer) or secured to the flange F in a variety of manners. The pipe P and flange F are exemplary in nature, and it will be appreciated that the sensor S can be integrated into/attached to a wide range of fluid transport/transmission/storage components including, but not limited to, pumps, valves, connectors, sampling connections, compressors, pressure relief devices, open-ended lines, welds, pipe joints, pressure readouts, plugs, gauges, turbines and couplings, containers or enclosures wrapped around joints and valves, etc., without departing from the scope of this disclosure. The sensor S can be secured to the pipe and/or pipe flange in a variety of manners, including the manners set forth herein. The manner in which a sensor or sensor array is secured depends at least in part on the equipment type and the conditions by which the equipment is intended to operate.

Figures 4A, 4B:
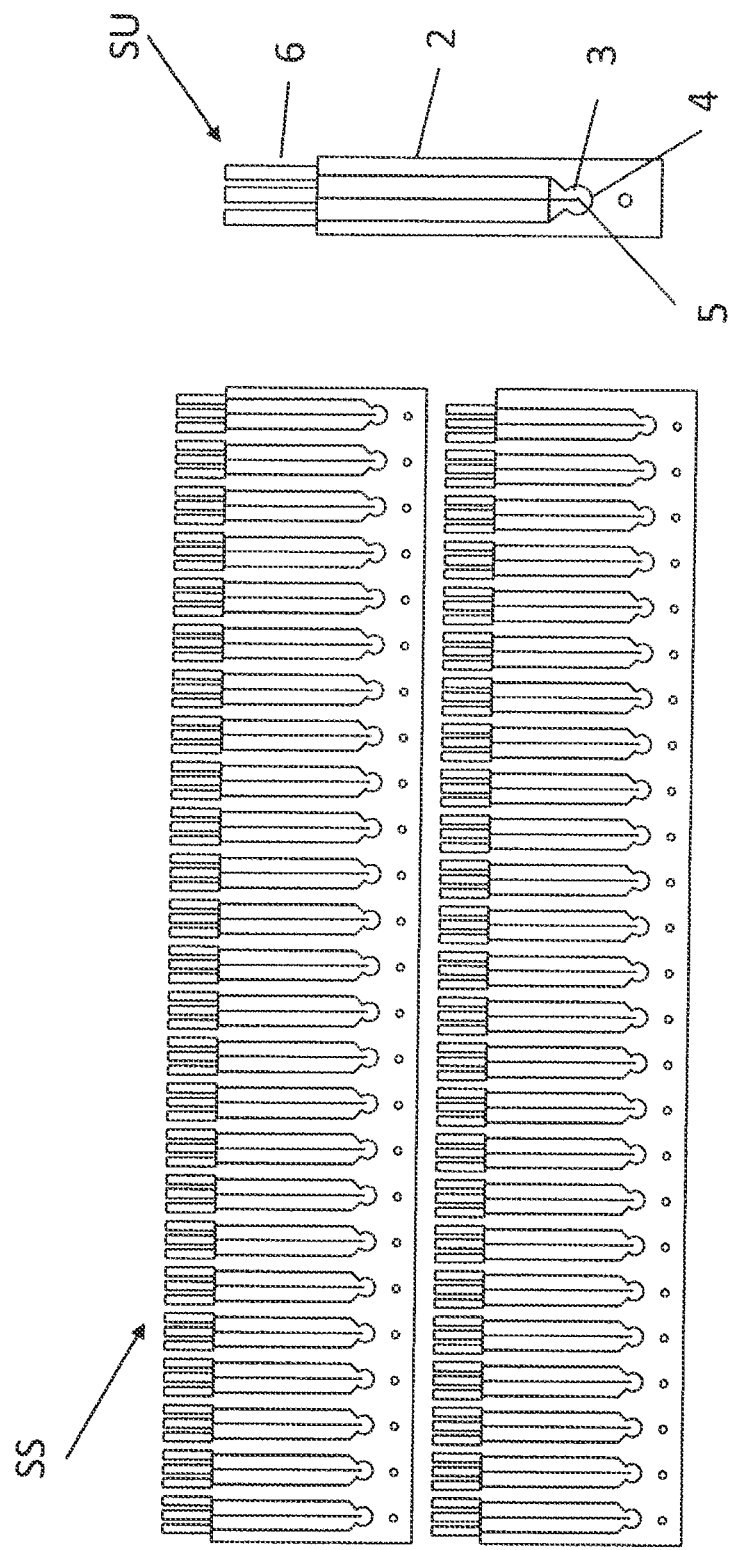
FIG. 4A illustrates an exemplary sensor array in accordance with the present disclosure.
FIG. 4B illustrates a single sensor in accordance with the present disclosure.

With reference to FIG. 4A, an exemplary sensor strip (array) SS is illustrated. The sensor strip SS includes a plurality of individual sensor units SU, as shown in detail in FIG. 4B. Each sensor unit SU includes a substrate (e.g., flexible, thin film, thick film and/or other materials appropriate for given application) 2 supporting a reference electrode 3, a working electrode 4, and a counter electrode 5. Conducting pads 6 are provided for coupling the electrodes to associated circuitry (e.g., processor, communication circuitry, etc.).

Figure 5:
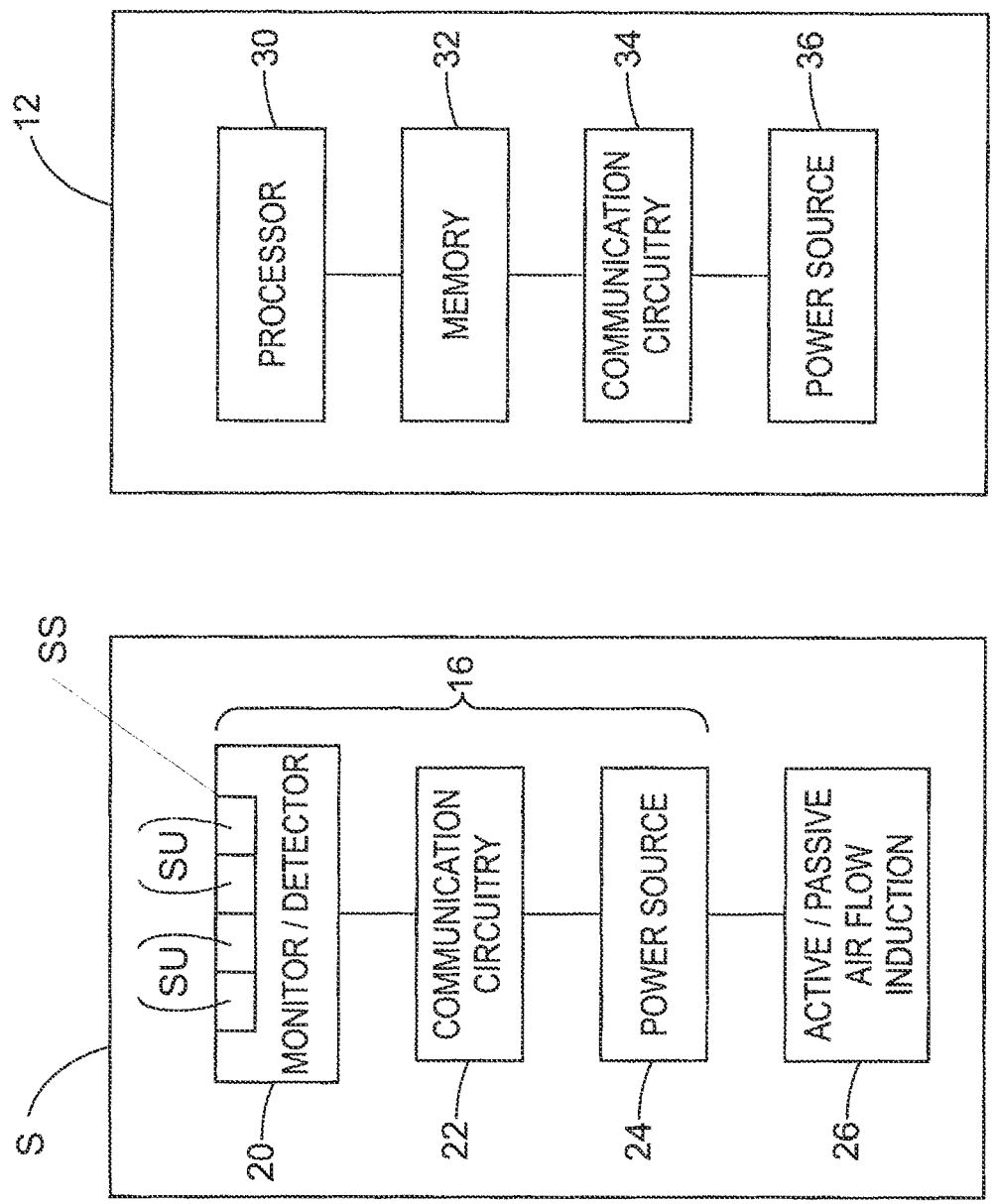
FIG. 5 is a schematic illustration of a sensor unit and remote monitoring device in accordance with the present disclosure.

In FIG. 5, a sensor S is schematically shown including a sensor strip SS. The sensor S generally includes a monitor/detector component 20, which includes a plurality of sensor units SU. As will be appreciated, any number of sensor units SU can be provided, and each sensor unit SU can be configured to detect a specific chemical. One monitor/detector component that is particularly well-suited for purposes of the present disclosure is set forth in U.S. Pat. No. 8,629,770 to Hummer et al. and U.S. Pat. No. 7,176,793 to Hummer, both of which are incorporated herein by reference in their entireties. Other types of monitor/detector components can also be used in accordance with the present disclosure.

The sensor S further includes communication circuitry 22 and a power source 24. The communication circuitry 22, in one embodiment, includes at least one of a near field communication device, Bluetooth communication device, WIFI communication device, or any other suitable communication circuitry for establishing communications with a remote processing device 12. The power source 24 can be a power supply such as a battery (lithium or other). In some cases the battery will be printed into the sensor along with the circuitry and electronics. In other embodiments, the power source 24 can be an antenna configured to receive energy wirelessly and supply the received energy to one or both of the monitor/detector component 20 and/or communication circuitry 22 such that no onboard battery is required for operation of the monitor system 16. Solar cells can also be used to provide power. An active or passive air flow induction device 26 can be provided for ensuring adequate and or continuous flow of air to the monitor/detector component 20. Such devices can include fans, micropumps, louvers, vents etc. An active induction device can be separately replaceable within the system and can include its own power supply. Alternatively, an active induction device can be configured to receive power from power supply 24 (or from power supply solar cells).

It should be appreciated that the monitor/detector component 20 can comprise a plurality of sensors strips SS. The sensor units SU and or strips SS can be individually replaceable or can be replaced as a unit. Replacement of the sensor units SU and/or strips SS may be necessary due to sensor degradation. In other situations, a user may wish to detect certain chemicals and will choose which sensors to install in the system. In one embodiment, the entire sensor S is replaceable as a unit.

The sensor units SU may detect a wide range of chemicals/materials/gasses. In the exemplary embodiment, the sensor units SS are configured to detect volatile organic compounds (VOCs) such as benzene, zylene and toluene for example, or any other chemical where leakage into the atmosphere or elsewhere is undesirable. It will be appreciated that the sensor S is configured to communicate with the remote processing device 12. That is, the sensor S collects data and transmits or otherwise shares the collected data with the remote processing device 12 for processing. The remote processing device 12 of the illustrated embodiment includes a processor 30, a memory 32, a communication circuitry 34, and a power source 36. It will be appreciated that the remote processing device 12 can include a wide variety of additional components as is conventional. Such additional components can include a display device, input device, various sensors, various antennas, etc. In some examples, the processor and memory can be onboard the sensor S. In one embodiment, precision ink-jet printing and/or screen printing is used to produce all or part of the sensor S.

Data collected by the monitor/detector component 20 is transmitted via communication circuitry 22 to communication circuitry 34 of the remote processing device 12. Other data, such as sensor state, status, performance data, and the like can also be transmitted to the remote processing device 12. Any suitable manner of transmitting the data from the sensor S to the remote processing device 12 can be employed.

The data collected and transmitted by the sensor S is then processed by the remote processing device 12 to detect one or more chemicals in accordance with one or more methods set forth in U.S. Pat. No. 8,629,770 to Hummer et al. and U.S. Pat. No. 7,176,793 to Hummer. To this end, suitable software for analyzing the data is stored in memory 32 of the remote processing device 12. Other detection and/or analyzing methods and techniques may also be used in conjunction with aspects of the present disclosure.

It will be appreciated that in some embodiments, the sensor S can include onboard processing and memory for performing onboard processing of the data generated by the sensor units SU. In such case, the sensor S software can be programmed and reprogrammed remotely to adjust sensor baselines (minimum detection level) and thresholds (maximum detection level). This remote reprogramming feature allows the system to evolve with the fast pace changes in standards, which are based on installed components and the technique by which the emissions are sampled to determine leaks and levels of unwanted emissions.

In one embodiment, the software stored in memory 32 can be in the form of an application, or "app", that is downloaded from an app store or the like. The app can be provided with various "signatures" of chemicals. The signatures can be compared to the data to determine whether the chemical signature was detected by the sensor system S. The app can be configured to be automatically updated with new signatures as the need to detect particular chemicals arise. That is, it is possible to provide new and/or additional chemical signatures for the app to check against the data to detect specific chemicals without changing the sensors or adding specific new sensors.

The app can further include features such as adjustable thresholds. For example, for some chemicals that are routinely present in certain amounts and/or not generally considered dangerous below certain levels, the application can be configured to detect or trigger an alarm when a threshold amount is met or exceeded. For some chemicals which are considered dangerous in any amount, the thresholds would not generally be adjustable. It will be appreciated that the application's underlying software can be reprogrammed to adhere to changing objectives (i.e. changes in levels of emissions, changes in operational tempo or capacity and new threats, etc.) For example, in some instances the level of emissions is tied to utilization and stress on the system. A system running at its highest capability may have increased leakage and may exceed the threshold amount. If operators choose to run systems at maximum levels, the sensor thresholds can be temporarily increased until a lower operational tempo resumes.

In some embodiments, the functioning sensor can be used to set the minimum baseline leakage under normal operating conditions. To this end, the sensor can be calibrated under normal operating conditions to determine a minimum baseline leakage, as some leakage is likely present and detectable under normal operating conditions. This baseline leakage value can be used to avoid/mitigate false alarms by establishing a normal operating leakage.

The app can be further configured to, once a chemical is detected, share the detection information. For example, the application can be configured to use the communication circuitry 34 to broadcast an alert (or generate a notification) via any suitable communications network (e.g., WIFI, NFC, Bluetooth, cell, etc.). The alert may be directly sent to other, for example, personal communication devices of maintenance personnel in the area, or may be sent to a server (or through a network) and then on to devices within a range of a given location. In one example, when an alert is triggered by the automatic sensor S, an operator with a hand-held device (e.g., a handheld device with sensing capabilities) can be dispatched to verify that the component is indeed emitting past the maximum threshold. In some examples, the alarm information can also be shared immediately with regulators or governing bodies that oversee the LDAR programs, and the governing bodies may offer incentives to the plant owner for sharing such information. The information could also be shared in an open source dashboard for the public to consume through analytics.

Providing the sensor S as a separate component selectively attachable to a fluid transmission component or the like allows for rapid deployment and/or replacement of the sensors S to existing pipeline, refinery etc. infrastructure. To this end, the present disclosure sets forth several attachment structures and configurations to meet the demands of various installations.

Figure 6:
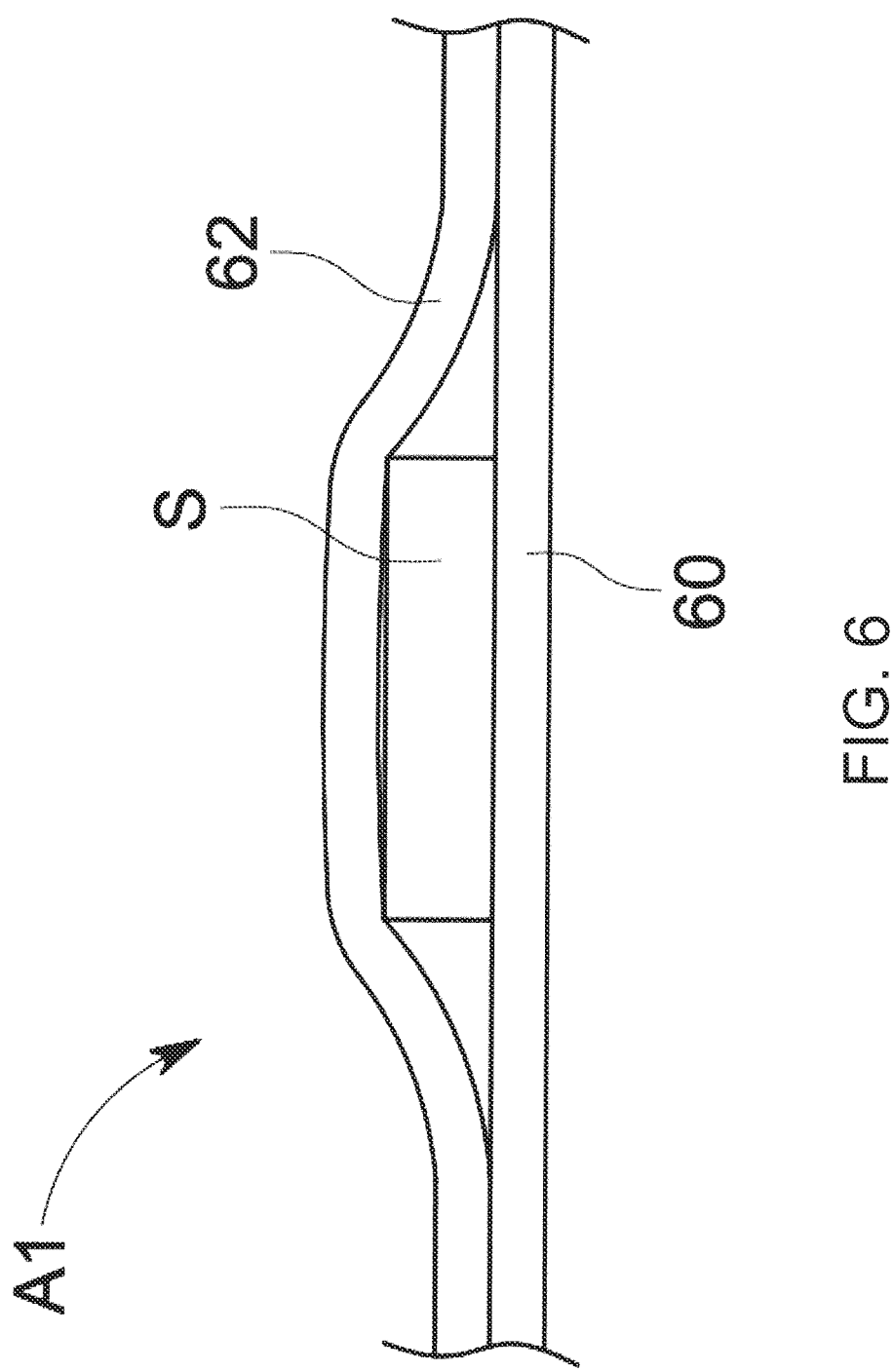
FIG. 6 is a cross-sectional view of a first strap attach assembly in accordance with the present disclosure.
Figure 7:
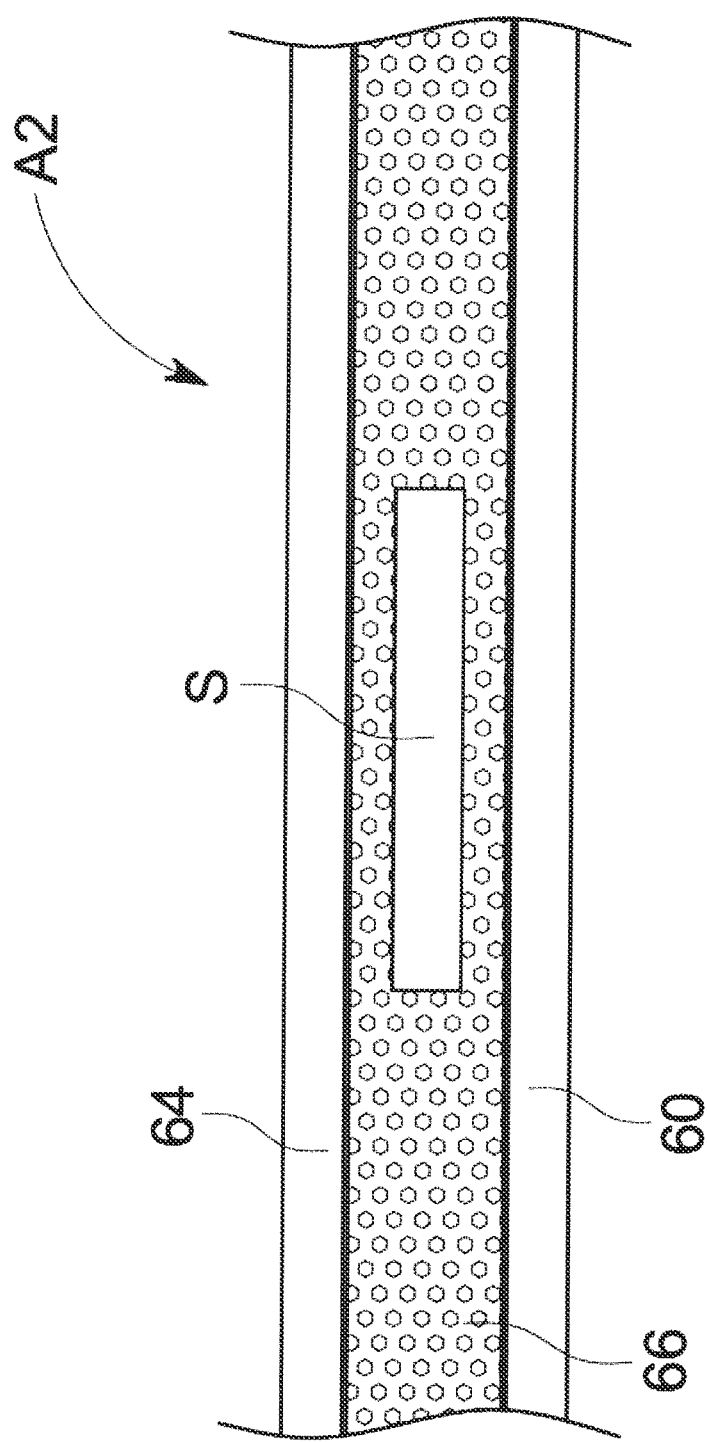
FIG. 7 is a cross-sectional view of a second strap attach assembly in accordance with the present disclosure.
Figure 8:
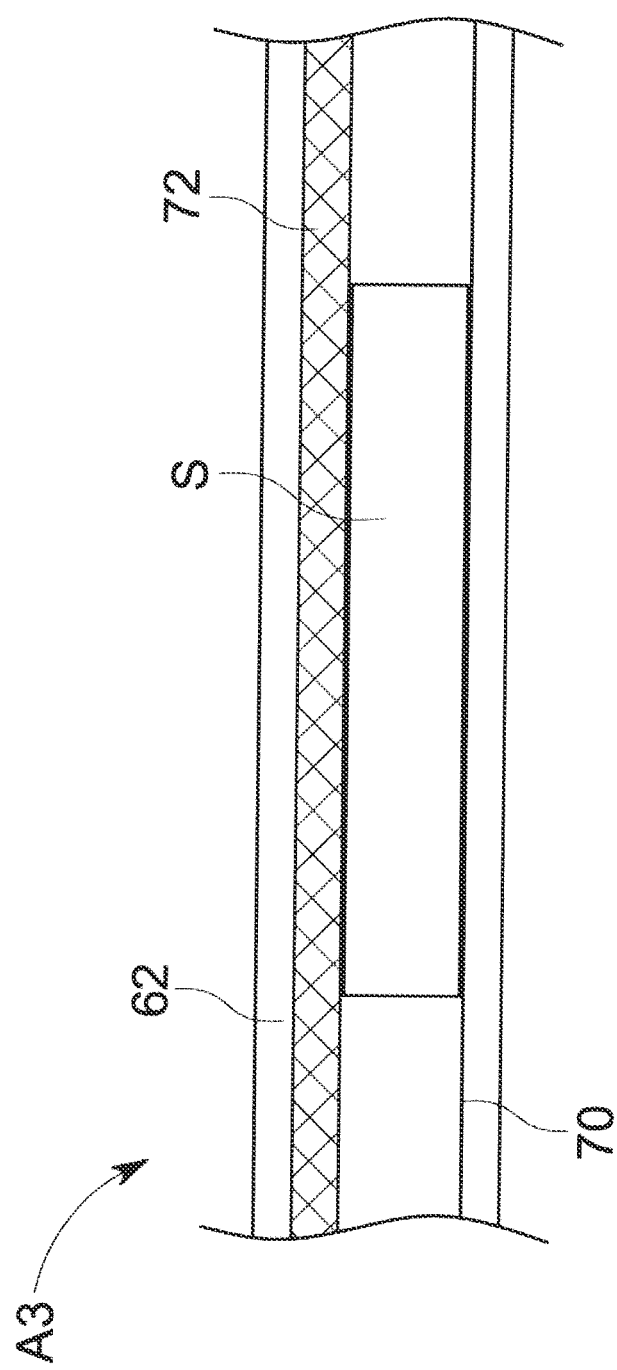
FIG. 8 is a cross-sectional view of a third strap attach assembly in accordance with the present disclosure.

Turning to FIGS. 6-8, three different flexible strap attach assemblies A1, A2 and A3 are shown. It should be appreciated that each assembly A1, A2 and A3 is configured to be wrapped around or otherwise closely engaged with a portion of a component to be monitored for chemicals of corrosion or leaks, or structure adjacent the component to be monitored for chemicals of corrosion or leaks. By providing the sensor S as part of these flexible strap attach assemblies, the sensor S can be readily affixed to a wide range of infrastructure. Each of the assemblies are shown in schematic partial cross-section to illustrate the various layers of each assembly. It should be appreciated that the strap can have any suitable length. In some examples, the strap can be adjustable and or can include perforations or other part lines to allow the length of the strap to be shortened.

In FIG. 6, the strap attach assembly A1 includes a base layer 60 of a material including a hook-and-loop fastener or other releasable securable fastener structure (e.g., adjustable clasp or clamp). An outer layer 62 of durable and/or flexible fabric sandwiches the sensor S with the base layer 60. The outer layer 62 can be impermeable, or can be water impermeable but still permit water vapor and/or other gasses to pass there through to optimize sensor functionality and protection. In still other examples, the outer layer 62 is permeable and breathable to an extent necessary for optimal sensor functionality. Regardless of the physical properties of the outer layer 62, the outer layer 62 and inner layer 60 support the sensor S there between.

In FIG. 7, the strap attach assembly A2 is similar to strap attach assembly A1 but includes a foam or sponge layer 66 in which the sensor S is at least partially enclosed. In other examples, the sensor S can be positioned between or suspended between a pair of, or multiple, foam or sponge (or any other material that holds liquid) elements. The foam or sponge layer 66 can provide cushioning to the sensor S and can act to absorb and/or concentrate leaking fluids or the like and allows for optimal functionality of the sensor. This can help aid in detection by the sensor S and can provide, in some instances, some amount of protection to the sensor S from the leaking fluid and/or other materials and/or conditions that would otherwise impede the functionality of the sensor.

In FIG. 8, the strap attach assembly A3 includes a fine mesh base layer 70 on which sensor S is supported. The mesh base layer 70 comprises a highly durable material that is resistant to extreme conditions. Outer layer 62 and a magnetic mesh layer 72 sandwich the sensor S along with layer 70. In this exemplary embodiment, the magnetic mesh layer 72 is used to magnetically secure the strap attach assembly A3 to steel pipe or other component. It should be appreciated that the sensor S can be provided on a magnetic substrate, such as a magnetic disk or puck or the like, such that it can be readily magnetically secured to a component. In addition to being fixated magnetically, the sensor itself can be made using magnetic nanoparticles, which is a class of nanoparticle that can be manipulated using magnetic fields. Other sensor components can be made of pulverized magnetic metals and printed magnetic inks, including the power source, sensors, electrical circuits and other components of the sensor system. One of the several magnetic inks that can be used includes neodymium.

Figure 9:
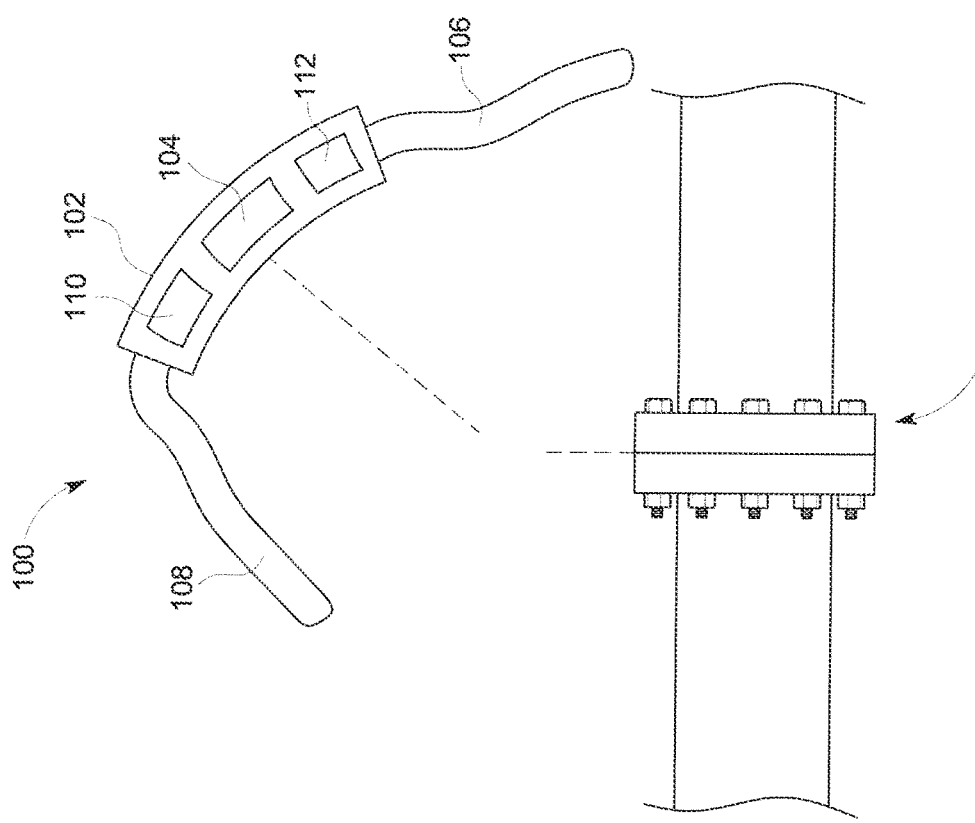
FIG. 9 is a perspective view of an exemplary monitoring system in the form of a flange band in accordance with the present disclosure.

FIG. 9 illustrates an exemplary monitoring system in the form of a flange band 100. The flange band 100 includes a main body portion 102 which includes a highly durable material that is resistant to extreme conditions and allows for optimal functionality of the sensor S that can include a fabric or the like, supporting a sensor array 104 in the manner described above. First and second straps 106 and 108 extend from the main body portion 102 and are configured to secure the flange band 100 about a pipe flange 120 (or other structure). As noted above, various attachment mechanisms (hook and loop, magnetic, D-rings, clamp, clasp, etc.) can be provided for securing the straps 106 and 108 about the pipe flange 120. In this embodiment, first and second solar cells 110 and 112 are also supported on the main body portion 102. The solar cells 110 and 112 can provide main or supplementary power to the sensor array and/or other components of the monitoring system 100. The flange band 100 can further provide protection to the flange 120 (or other component) from corrosion or damage from exposure to the environment.

Figure 10:
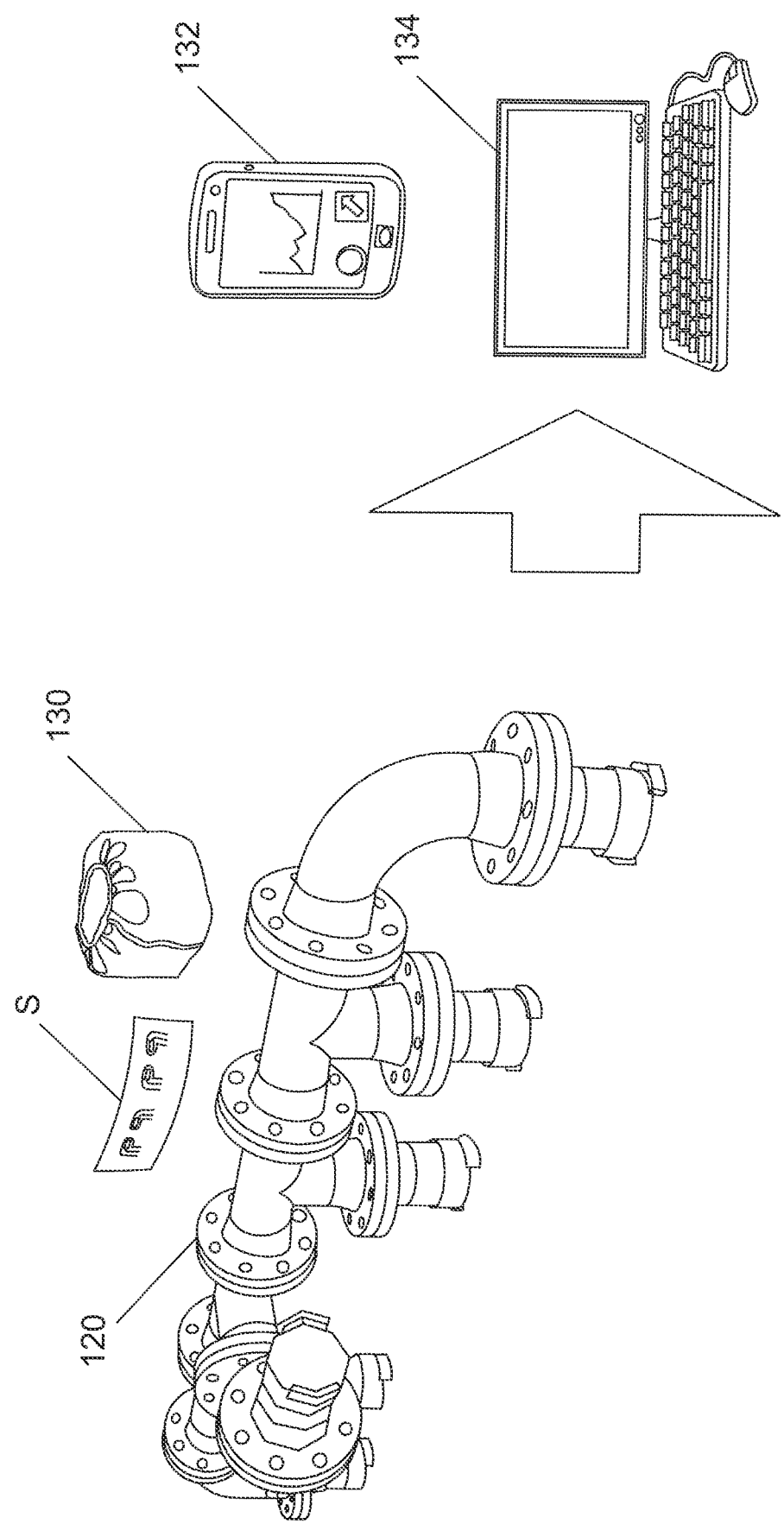
FIG. 10 is a perspective view of an exemplary system in accordance with the present disclosure.

FIG. 10 illustrates an exemplary pipe structure (or basic portion of a chemical processing plant or other facility). A flange band 130 is shown separate from a sensor S. The sensor S will be supported by the flange band 130 in proximity to a pipe flange or the like for monitoring the same. As will be appreciated, the sensor S is configured to communicate with one or more receivers, which in this embodiment include a mobile phone 132 (or wearable device) and/or a laptop 134. FIGS. 11-15 illustrate various exemplary flange bands A4-A9 for securing a sensor S to a component, such as the pipe flanges of FIG. 10, or other structures. The flange band can be made of highly elastic and durable structured material such as expandable graphite, graphene, composite particles, polymers and elastomers capable of fitting a wide range of pipes, pipe connectors and joints. The flange bands are made of rugged materials that allow them to properly fit a wide range of pipe sizes. In some embodiments, the flange band has a zipper compartment where the sensor can be deposited for easy access and replacement. The zipper pocket is made of suitable materials and has an operable environment that allows the sensor to function at an optimal level.

In some embodiments, the one or more of the following materials can be used for the flange bands (or portions thereof): nanofibers, polymers, elastomers, large macroscopic materials built in a spider-web like, highly expandable and flexible polyimide substrates that is engineered in a way to allow unique area dilatations. Other possibilities include: microlattice, graphene, self-healing plastic and other highly rugged and permeable materials.

Figure 16:
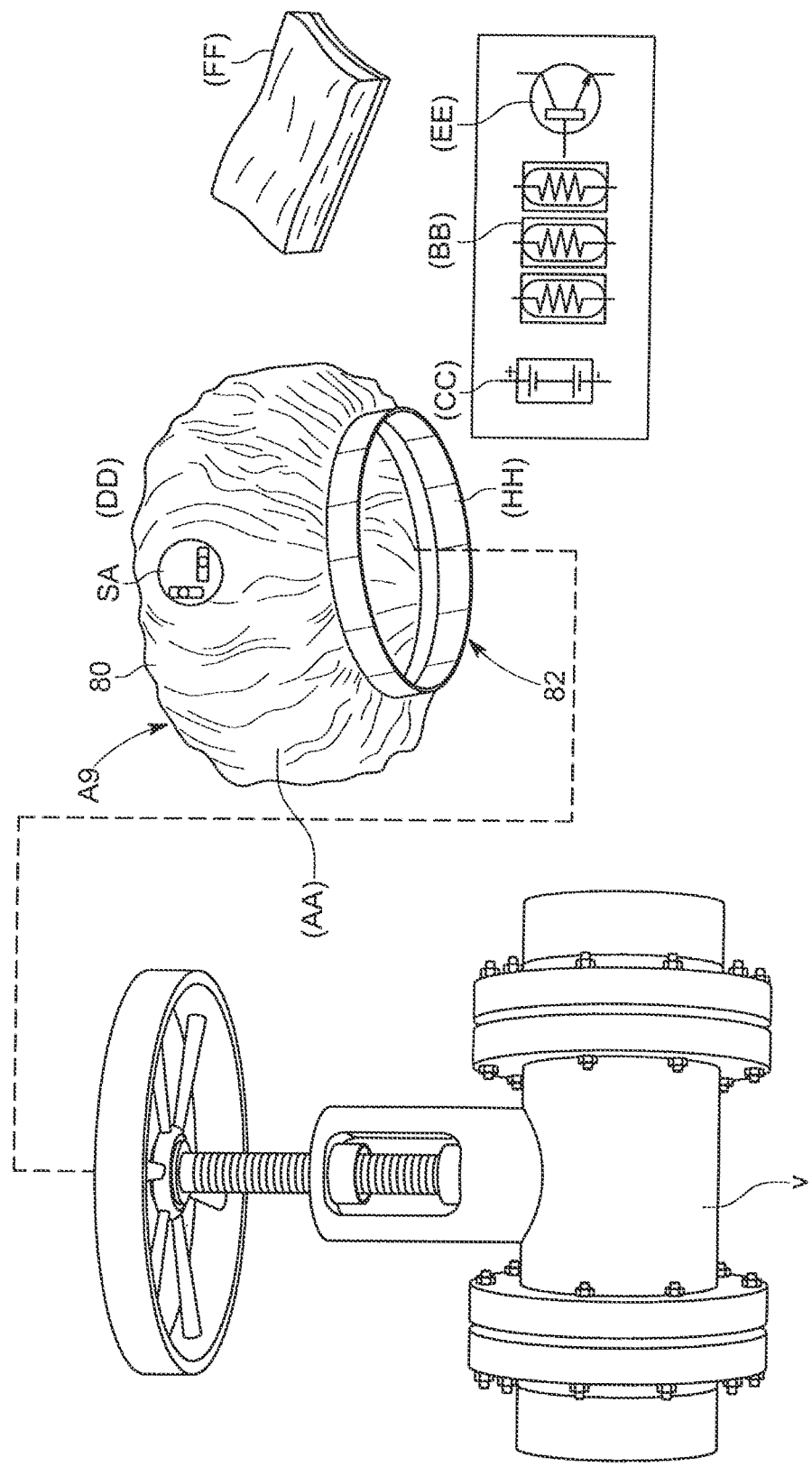
FIG. 16 is a perspective view of an attachment device in accordance with the present disclosure in the form of a bonnet for securing a sensor to a valve component.

Turning to FIG. 16, yet another attachment device A9 is illustrated. In this embodiment, the attachment device includes a bonnet 80 of flexible and/or elastic material in which sensor S is supported. Bonnet 80 can be an impermeable material such as plastic or the like, or can be semi-permeable or fully permeable, or otherwise configured for optimal functionality. In some examples, the bonnet can be waterproof but still allow water vapor to pass through. The attachment device A includes a durable covering AA, a sensor array SA, a power source CC, an indicator light DD, an encrypted serial number EE, a foam/sponge layer FF, and an elastic strip HH.

Bonnet 80 is configured to be telescoped over at least a portion of a component, such as a valve V or the like. To this end, the bonnet 80 includes an elastic or otherwise resilient opening 82. The opening 82 can be enlarged to pass over a certain portion of the valve, such as a knob, lever, wheel or other actuator. In one example, the opening includes an elastic band. In another example, the opening includes a drawstring or other member for drawing the opening tight, but also allowing the opening to be enlarged for installation. As will be appreciated, a clamp, clasp or tie can be fastened about the base of the bonnet 80 to secure it to the component being monitored.

The sensor S can be supported by the bonnet 80 as illustrated, or can be supported in any other suitable location by the bonnet 80. The bonnet 80 can be configured to trap and/or concentrate any leaking fluids to aid in detection by the sensor S. The bonnet 80 can be constructed of transparent material to allow indicator lights of the sensor S to be viewed when the bonnet 80 is installed. In some applications, the valve V can continue to be actuated without removal of the bonnet 80 therefrom. This can permit detection of leaks in the valve V that only occur when the valve is in a particular state (e.g., fully open, partially open, fully closed). The sensor(s) S can also be embedded or part of the material by which the bonnet 80 is made constructed. Such material is most suitable for the functionality of the sensor device in relation to the operating valve or component size and related conditions.

One function of the bonnet (container) is to trap leakage or unwanted emissions from a monitored component for improved detection. To this end, the bonnet can be coated with certain materials to keep the gas or other leakage contained in the bonnet. The certain materials could be used for both flange bands as well as valve covers (e.g. bonnet). Certain materials that may be absorbent and/or useful for trapping and/or containing leakage of gasses or liquids include tenax, silica gel, coconut charcoal and graphitized carbon black, etc. In other examples, cloth made of graphene or nanotubes with embedded sensor electrodes can be used. In these examples, the flange bands and/or valve bonnets can be made of flexible graphene electrode cloth. At just one atom thick, graphene is a very thin substance capable of conducting electricity. It is very flexible and is one of the strongest materials. These properties make graphene well-suited for this application.

Figure 17:
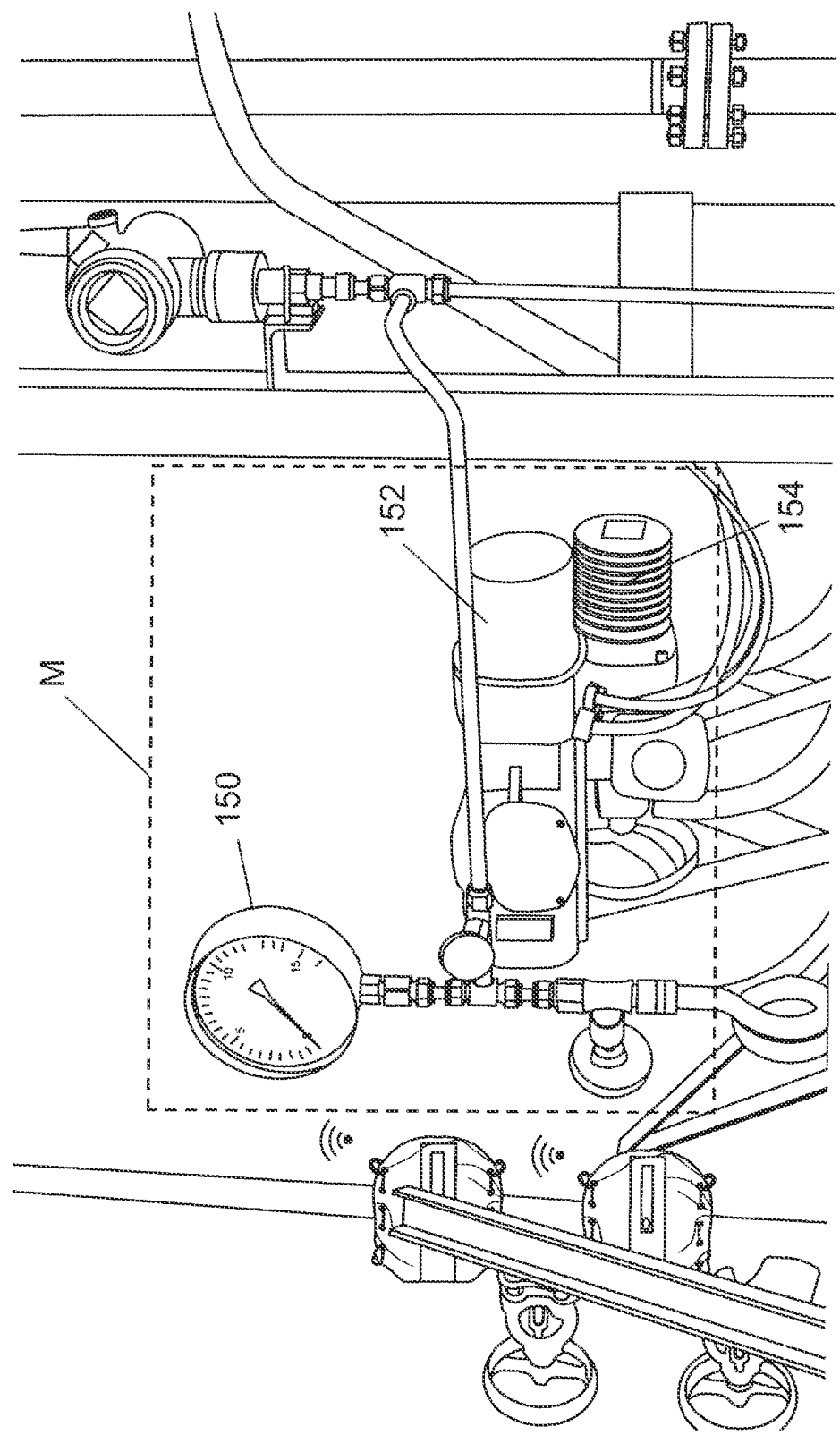
FIG. 17 is a perspective view of yet another attachment device in accordance with the present disclosure for securing a sensor to a target component.

Turning to FIG. 17, another exemplary embodiment of the present disclosure is illustrated wherein a sensor S is supported in a mesh sock M or other covering that is draped over a target component, which in this embodiment includes a gauge 150 and adjacent valves 152 and 154.

Figure 18:
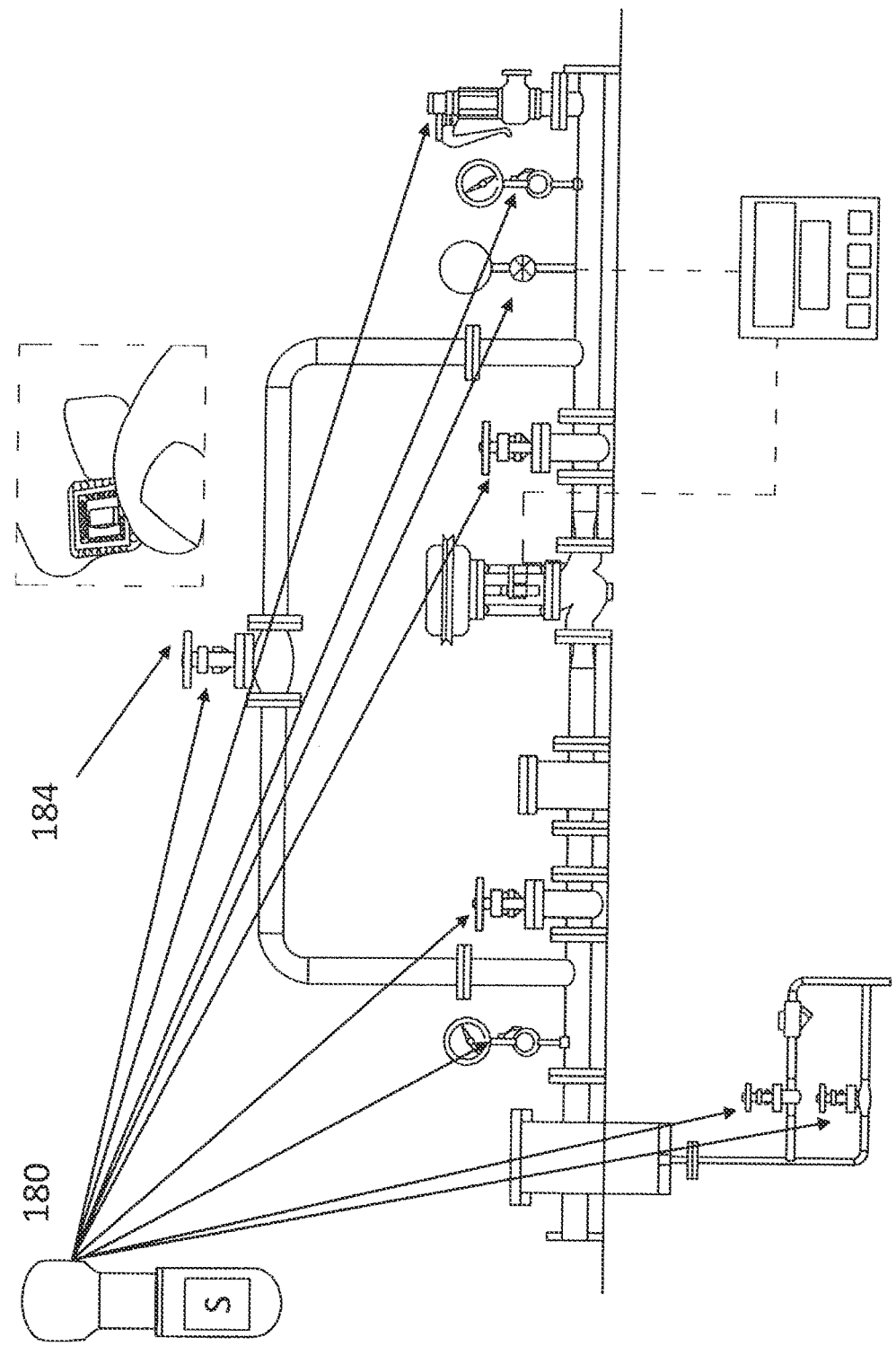
FIG. 18 is a perspective view of still another attachment device in accordance with the present disclosure for securing a sensor to a target component.

In FIG. 18, a wire padlock tamper evident safety lock 180 includes a sensor S in accordance with the present disclosure. As will be appreciated, the safety lock can be used to lock a component, such as a valve 184. The safety lock 180 includes sensor S, but otherwise is identical to and can be used in the same manner as, any conventional safety lock 180.

Figure 19:
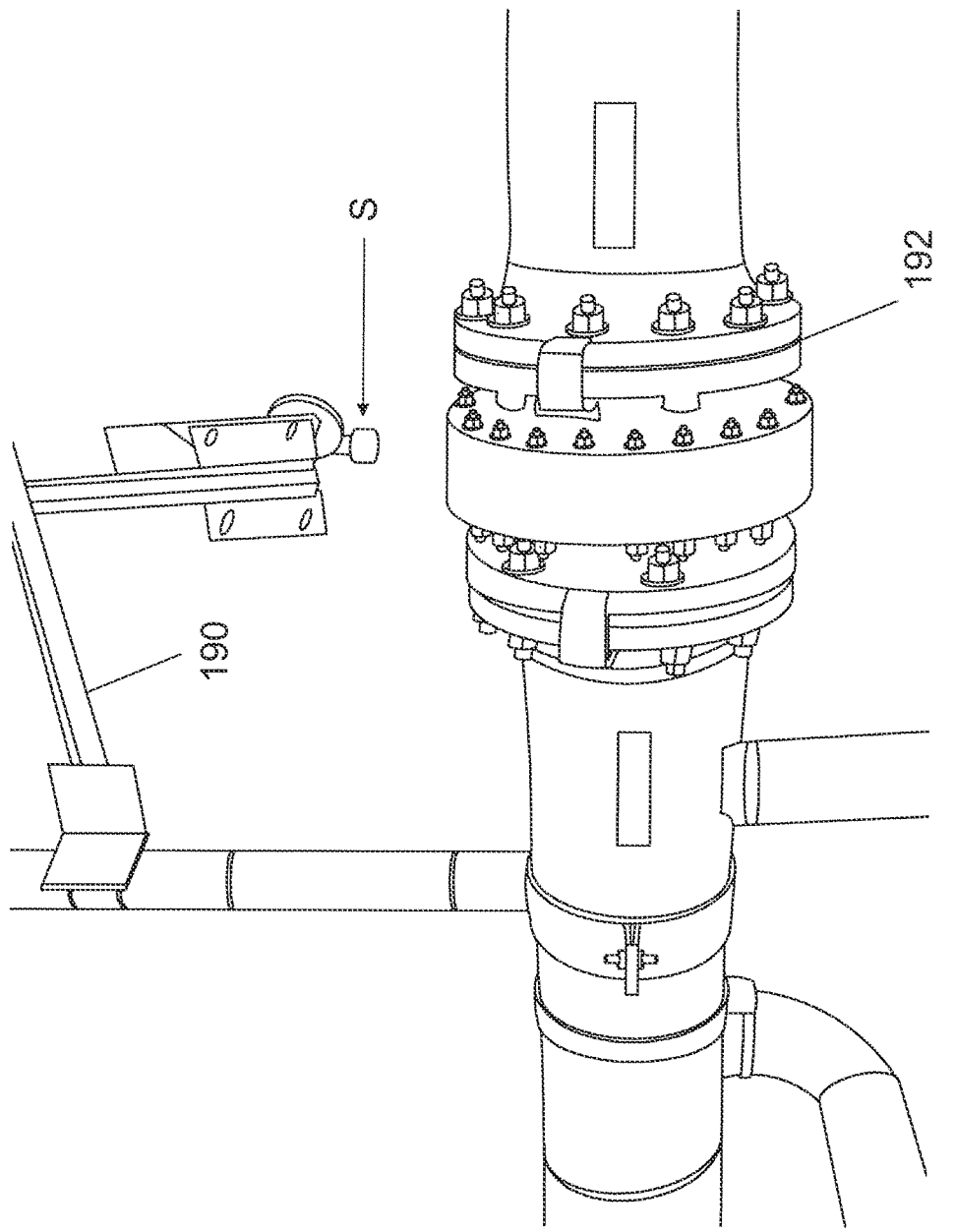
FIG. 19 is a perspective view of an independent mount for a sensor in accordance with the present disclosure.
Figure 20:
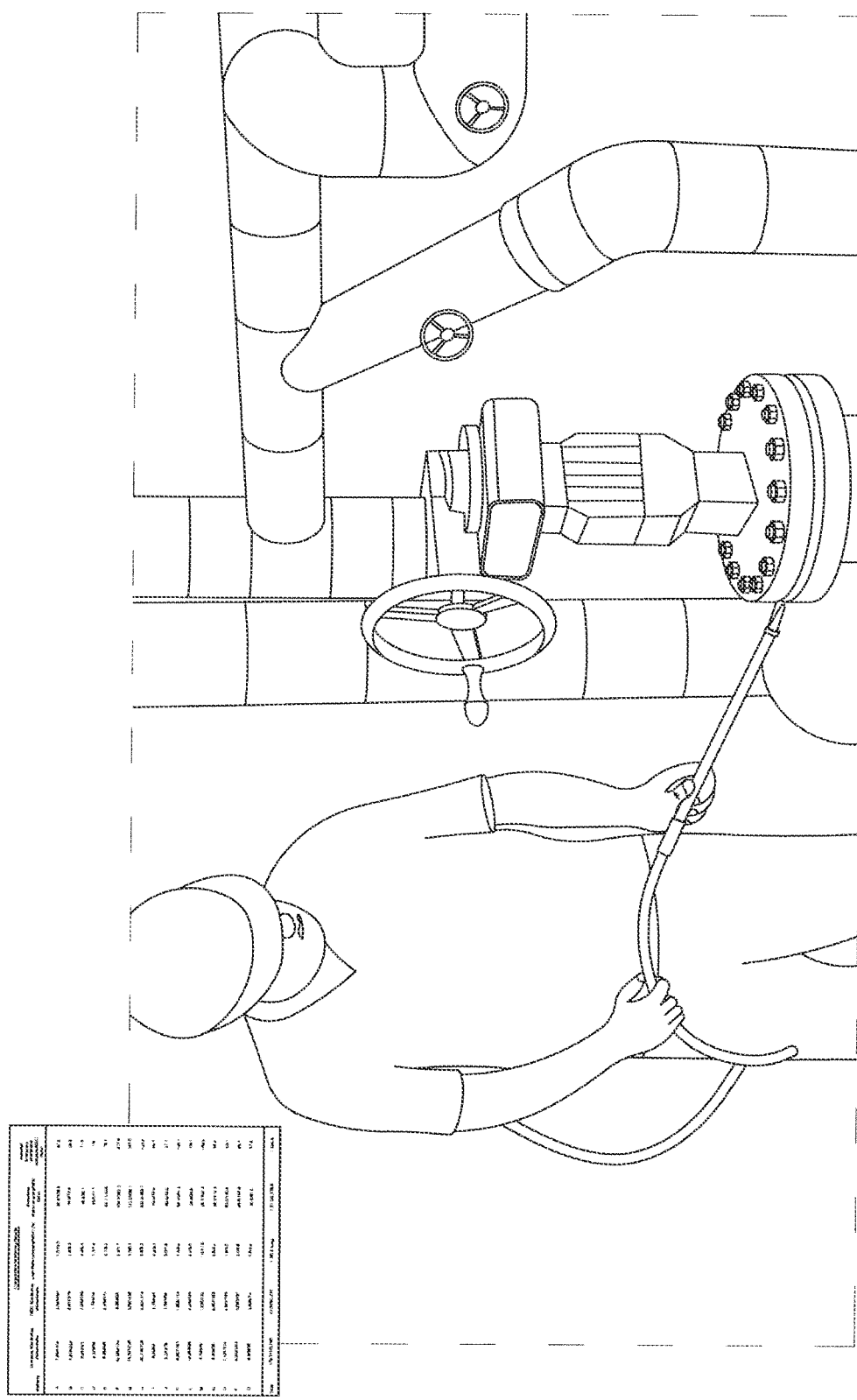
FIG. 20 illustrates a prior art method of testing a target component for unwanted emissions.

In FIG. 19, a sensor S is supported by an independent mount 190 in position over or under or nearby a pipe flange (or other component) 192. This arrangement can be useful when a direct attach (e.g., flange band or bonnet, etc.) is impractical or undesirable.

In some application environments, such as refineries and pipeline infrastructure, the sensor array will be focused mostly on the detection of benzene, xylene and toluene among other VOCs and HAPs identified by the EPA. Such chemical may typically be present in these environments at levels that, although detectable by the sensor array, may not be cause for taking corrective action. As such, the sensor arrays will be configured to sample the environments periodically and to report detected concentrations of the chemicals periodically. Accordingly, the system will require adequate power to perform the periodic testing and/or reporting. In one example, a solar power supply is provided. The solar power supply can include one or more photovoltaic cells and one or more batteries for storing solar energy for use by the sensors and/or communication circuitry. In some embodiments, the solar cells and/or batteries can be integral with the monitoring system. In this regard, for example, certain portions of the monitoring system can be fitted with solar cells (e.g., a housing or other enclosure, the bonnet fabric, etc.) In other embodiments, the solar cells and/or batteries can be external to the monitoring system (e.g., separate unit located in position exposed to the sun and electrically coupled to the monitoring system. Solar power is particularly well-suited to pipeline applications having remote sensing locations where other power supplies (e.g., line power) are not practical. Power can also be provided or harvested from other sources, such as wind, hydro, thermal, wireless, inductive, etc). The system can also have the capability to switch power sources (i.e. internal, external or natural) based on the operational requirements and power demands.

It should now be appreciated that aspects of the present disclosure overcome many if not all of the shortcomings of manual LDAR programs. For example, with manual sampling done by a human operator there are other factors that have the potential to bias results. There is the possibility that the human operator did not calibrate the equipment properly based on the target piece of equipment. There is the possibility that the human operator failed to properly sample the target piece of equipment. There is also the possibility of sample bias or temporary high reading based on unusually high pressure in the system. This is a condition that doesn't always prevail. In other words, the real-time monitoring of the present disclosure can perform constant monitoring, rather than a snap shot in a moment in time. This gives the plant operator much more information with which to make maintenance decisions.

The exemplary embodiments have been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A monitoring system for monitoring chemicals in an environment comprising:
a sensor including a detector component operative to generate data in response to the presence or absence of one or more chemicals or concentration level of one or more chemicals, communication circuitry and a power source operatively coupled to the detector component and the communication circuitry for supplying power thereto, the communication circuitry configured to transmit data generated by the detector component to an associated receiver;
wherein the monitoring system is placed near chemical components prone to corrode or near components prone to develop unwanted emissions, said components having an interior chamber for transmitting or storing a fluid or gas;
wherein the sensor further determines at least one of a location or operating status of the sensor, the communication circuitry configured to transmit at least one of the location or operating status to the associated receiver; and
wherein the detector component includes at least one micro-electro-mechanical systems sensor.

2. The monitoring device of claim 1, further comprising one or more induction device or component or element for actively or passively directing substances towards or away from the detector component.

3. The monitoring device of claim 1, wherein the chemical component prone to corrode or develop unwanted emissions includes at least one of a fluid or gas extraction, processing, storage or transmission component.

4. The monitoring device of claim 1, wherein the chemical component prone to corrode or develop unwanted emissions includes a valve, and wherein the monitoring system further comprises a bonnet telescopable over an actuator of the valve.

5. The monitoring device of claim 4, wherein the bonnet comprises a flexible material or stretchable substrate with elastic or insulative properties or a combination thereof adapted to cover or conform to the outer surface of a valve and to trap or concentrate one or more chemicals emanating from the valve for optimal measuring by the detector component.

6. The monitoring device of claim 5, wherein the bonnet is comprised of flexible power source layer, flexible printed circuit board layer comprised of communication circuitry and at least one detector component.

7. The monitoring device of claim 3, wherein the component of fluid or gas extraction, processing, storage or transmission includes a pipe flange, and the monitoring device further configured to releasably secure the sensor to an independent mount near the pipe flange.

8. The monitoring device of claim 7, wherein the sensor is configured to use measurements of humidity, temperature and other environmental and chemical characteristics to calibrate the sensor.

9. The monitoring device of claim 1, wherein the power source includes at least one of a solar cell or a battery.

10. The monitoring device of claim 1, wherein the power source includes an antenna configured to receive energy wirelessly and supply the received energy to at least one of the detector component or the communication circuitry.

11. A method of monitoring multiple chemical components prone to corrode or prone to develop unwanted emissions for unwanted emissions from one or more of the components, the method comprising:
provinding a plurality of sensors, each sensor including:
a detector component operative to generate data in response to the presence or absence of one or more chemicals;
communication circuitry;
and a power source operatively coupled to the detector component and the communication circuitry for supplying power thereto, the communication circuitry configured to transmit data generated by the detector component to an associated receiver;
associating each sensor with each component to be monitored; monitoring each component with its associated sensor over a period of time; and
transmitting data generated by each sensor to a receiver;
wherein each component has an interior chamber for extracting, processing, transmitting or storing a fluid or gas, and wherein each sensor is located near chemical components prone to corrode or near components prone to develop unwanted emissions for detecting unwanted emissions of a fluid or gas from within the chamber;
wherein at least one of the sensors further determines at least one of a location or operating status of the sensor, the communication circuitry configured to transmit at least one of the location or operating status to the associated receiver; and
wherein the detector component includes at least one micro-electro-mechanical systems sensor.

12. The method of claim 11, wherein the components to be monitored include at least one of a fluid or gas extracting, processing, transmitting or storage component.

13. The method of claim 12, wherein the fluid or gas transmission component includes a valve, and wherein the associating the sensor with each component includes configuring the sensor in a safety lock associated with each component.

14. The method of claim 13, further comprising actively or passively inducing at least a portion of the unwanted emission towards and away from the sensor in the safety lock.

15. The method of claim 11, further comprising securing each sensor in a location near at least one component prone to corrode or near at least one component prone to develop unwanted emissions.

16. The method of claim 15, wherein the sensor is configured to releasably secure the to a mount independent of the component being monitored.

17. The method of claim 11, wherein the sensors are configured to sense a concentration of the one or more chemicals, generate data indicative of the sensed concentration, periodically report a sensed concentration over a period of time and generating an alert if a sensed concentration exceeds a threshold concentration.

18. A component for fluid or gas transmission or storage comprising: an interior chamber for transmitting or storing a fluid or gas; and
a sensor including a detector component operative to generate data in response to the presence or absence of one or more chemicals or concentration level of one or more chemicals, communication circuitry and a power source operatively coupled to the detector component and the communication circuitry for supplying power thereto, the communication circuitry configured to transmit data generated by the detector component to an associated receiver;
wherein a monitoring system is placed near chemical components prone to corrode or near components prone to develop unwanted emissions, said components having an interior chamber for transmitting or storing a fluid or gas; and
wherein the detector component includes at least one micro-electro-mechanical systems sensor.

19. The monitoring device according to claim 18, further comprising one or more induction device or component or element for actively or passively directing substances towards or away from the detector component.

20. The component according to claim 18, wherein the component is one of a control device, flow conduit, pipe, pressure fitting, pressure relief device, drain, pump, plug, gauge, connector, compressor, pressurizer, open-ended line, closed-ended line, pipe joint, pipe flange, valve, vent, coupling, seal, wellhead, container, turbine, engine, tubing or other equipment or components subject to leak detection and repair regulations or used for extracting, refining, processing, filtration, distillation, mixing, separation, heating, cooling, fermentation, flow, transmission and insulation.

* * * * *